(12) United States Patent
Mysore et al.

(10) Patent No.: US 8,026,398 B2
(45) Date of Patent: *Sep. 27, 2011

(54) CATALYSTS COMPRISING A COMBINATION OF OXIDIZED METALS AND A METHOD FOR CLEAVING PHENYLALKYL HYDROPEROXIDES USING THE CATALYSTS

(76) Inventors: Narayana Mysore, Houston, TX (US); John Charles Saukaitis, Katy, TX (US); John Anthony Smegal, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/300,840

(22) PCT Filed: May 14, 2007

(86) PCT No.: PCT/US2007/068860
§ 371 (c)(1),
(2), (4) Date: Apr. 22, 2009

(87) PCT Pub. No.: WO2007/137021
PCT Pub. Date: Nov. 29, 2007

(65) Prior Publication Data
US 2010/0063326 A1    Mar. 11, 2010

Related U.S. Application Data

(60) Provisional application No. 60/747,361, filed on May 16, 2006.

(51) Int. Cl.
*C07C 45/00* (2006.01)
*B01J 23/00* (2006.01)

(52) U.S. Cl. ........ 568/385; 568/793; 502/325; 502/328; 502/338; 502/349

(58) Field of Classification Search .................. 568/385, 568/798; 502/325, 328, 338, 349
See application file for complete search history.

(56) References Cited

U.S. PATENT DOCUMENTS

| | | | |
|---|---|---|---|
| 2,757,209 A | 7/1956 | Joris | 260/621 |
| 3,305,590 A | 2/1967 | Pollitzer et al. | 260/621 |
| 3,928,477 A | 12/1975 | Field et al. | 260/621 |
| 4,173,587 A | 11/1979 | Wu et al. | 260/593 |
| 4,209,465 A | 6/1980 | Austin et al. | 568/385 |
| 4,210,606 A | 7/1980 | Austin et al. | 568/385 |
| 4,246,203 A | 1/1981 | Wirth | 568/385 |
| 4,262,153 A | 4/1981 | Velenyi et al. | 568/798 |
| 4,267,380 A | 5/1981 | Austin et al. | 568/385 |
| 4,310,712 A | 1/1982 | Langley | 568/798 |
| 4,328,377 A | 5/1982 | Mori et al. | 568/798 |
| 4,358,618 A | 11/1982 | Sifniades et al. | 568/385 |
| 4,480,141 A | 10/1984 | Drake | 568/798 |
| 4,487,970 A | 12/1984 | Drake | 568/342 |
| 4,490,565 A | 12/1984 | Chang et al. | 568/798 |
| 4,490,566 A | 12/1984 | Chang et al. | 568/798 |
| 4,743,573 A | 5/1988 | Romano et al. | 502/64 |
| 4,849,387 A | 7/1989 | Romano et al. | 502/64 |
| 4,870,217 A | 9/1989 | Knifton | 568/798 |
| 4,876,397 A | 10/1989 | Knifton et al. | 568/798 |
| 4,898,987 A | 2/1990 | Knifton | 568/385 |
| 4,898,995 A | 2/1990 | Knifton et al. | 568/798 |
| 5,245,090 A | 9/1993 | DeCaria et al. | 568/798 |
| 5,254,751 A | 10/1993 | Zakoshansky | 568/798 |
| 5,371,305 A | 12/1994 | Hood | 568/798 |
| 5,463,136 A | 10/1995 | Blackbourn et al. | 568/385 |
| 5,530,166 A | 6/1996 | Zakoshansky et al. | 568/798 |
| 5,668,075 A | 9/1997 | Milam et al. | 502/338 |
| 6,077,419 A | 6/2000 | Wittenbrink et al. | 568/798 |
| 6,169,215 B1 | 1/2001 | Levin et al. | 568/798 |
| 6,169,216 B1 | 1/2001 | Levin et al. | 342/357.13 |
| 6,225,513 B1 | 5/2001 | Zakoshansky et al. | 568/798 |
| 6,284,927 B1 | 9/2001 | Druliner et al. | 568/342 |
| 6,297,406 B1 | 10/2001 | Levin et al. | 568/798 |
| 6,410,804 B1 | 6/2002 | Levin et al. | 568/798 |

FOREIGN PATENT DOCUMENTS

| | | |
|---|---|---|
| EP | 125065 | 11/1984 |
| EP | 125066 | 11/1984 |
| EP | 638534 | 2/1995 |
| EP | 1398080 | 3/2004 |
| SU | 992508 | 1/1983 |
| SU | 551859 | 6/1995 |
| WO | WO2004108641 | 12/2004 |

*Primary Examiner* — Sikarl Witherspoon

(57) ABSTRACT

Catalyst comprising a combination of oxidized metals and processes for cleaving phenylalkyl hydroperoxides in the presence of the catalyst.

18 Claims, 2 Drawing Sheets

CATALYSTS COMPRISING A COMBINATION OF OXIDIZED METALS AND A METHOD FOR CLEAVING PHENYLALKYL HYDROPEROXIDES USING THE CATALYSTS

The present application claims priority to U.S. Provisional Patent Application 60/747,361 filed 16 May 2006.

FIELD OF THE INVENTION

The present application relates to catalysts comprising a combination of oxidized metals and to methods for cleaving one or more phenylalkyl hydroperoxides using the catalysts.

BACKGROUND OF THE INVENTION

Hydroxybenzenes have a wide variety of industrial uses. A number of processes are currently available for the production of hydroxybenzenes. One such process is known as a "cumene process."

A cumene process begins with the production of cumene from benzene and propylene. The cumene is then oxidized to form cumene hydroperoxide:

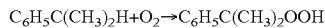

The cumene hydroperoxide subsequently is cleaved into phenol and acetone:

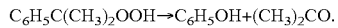

The oxidation of other phenylalkyl hydroperoxides generally follows a similar pathway.

The process also generally produces a number of byproducts. In a cumene process, byproducts may include, for example, α-methylstyrene (AMS), acetophenone, dicumylperoxide, and dimethylbenzyl alcohol (DMBA). Less desirable byproducts include, for example, AMS dimer and cumyl phenol (CP).

On an industrial scale, cumene hydroperoxide typically is catalytically cleaved with dilute sulfuric acid at relatively high temperatures. The use of dilute sulfuric acid has a number of disadvantages. One disadvantage is that DMBA tends to dehydrate to AMS. AMS tends to form unwanted byproducts, including but not necessarily limited to AMS dimer and cumyl phenol (CP). Although it is possible to thermally crack AMS dimer and CP to produce AMS and phenol, yields are poor and a substantial amount of labor and equipment are required.

U.S. Pat. No. 6,297,406 describes a process for producing phenol and acetone from cumene hydroperoxide in which the cumene hydroperoxide is contacted with a solid-acid catalyst. The solid-acid catalyst comprises a mixed oxide of cerium and a Group IVB metal. In the examples, the catalyst is used under highly dilute laboratory conditions, including a high initial concentration of acetone and dropwise addition of cumene hydroperoxide.

Dropwise addition of cumene hydroperoxide into a relatively large volume of diluent may produce a number of advantages. For example, the drops of cumene hydroperoxide are expected rapidly to convert to phenol and acetone after addition to the large volume of diluent, and the accumulation of less desirable byproducts (cumyl phenol, dimers of AMS) should be minimized or avoided.

Unfortunately, it is not feasible to produce a large volume of phenol by dropwise addition of cumyl hydroperoxide to a large volume of diluent. The yield of phenol produced by such a process would be too low relative to the labor and equipment that would be required to handle the large volume of diluent.

Catalysts and methods of using catalysts are needed which efficiently cleave phenylalkyl hydroperoxides to produce phenol at high yields relative to the materials being processed.

SUMMARY OF THE INVENTION

The present application provides a catalyst comprising a combination of oxidized metals.

The present application provides a catalyst comprising: a combination comprising a first amount of oxidized first metal and a second amount of oxidized second metal; wherein the first metal is selected from the group consisting of tin, iron, zinc, bismuth, and combinations thereof and the second metal is selected from the group consisting of zirconium, antimony, tungsten, and combinations thereof.

The present application also provides a catalyst comprising oxidized forms of a combination of metals selected from the group consisting of: tungsten and tin; tungsten and iron; tungsten and cerium; tungsten and bismuth; tungsten and zinc; zirconium and tin; and, antimony and tin.

The present application provides a process for cleaving phenylalkyl hydroperoxides using catalyst comprising a combination of oxidized metals.

The present application also provides a process for cleaving phenylalkyl hydroperoxides comprising: feeding a phenylalkyl hydroperoxide feed and a ketone feed to a reactor in a continuous process to produce a cleavage reaction mixture, the reactor containing catalyst comprising a combination of oxidized metals; and, subjecting the cleavage reaction mixture to cleavage conditions in the presence of the catalyst, the cleavage conditions being effective to cleave phenylalkyl hydroperoxide and to produce a cleavage product comprising one or more hydroxybenzenes and one or more ketones.

BRIEF DESCRIPTION OF THE DRAWINGS

One or more embodiments of the invention are described in detail and by way of example with reference to the accompanying drawings.

DETAILED DESCRIPTION OF THE INVENTION

Figure 1:
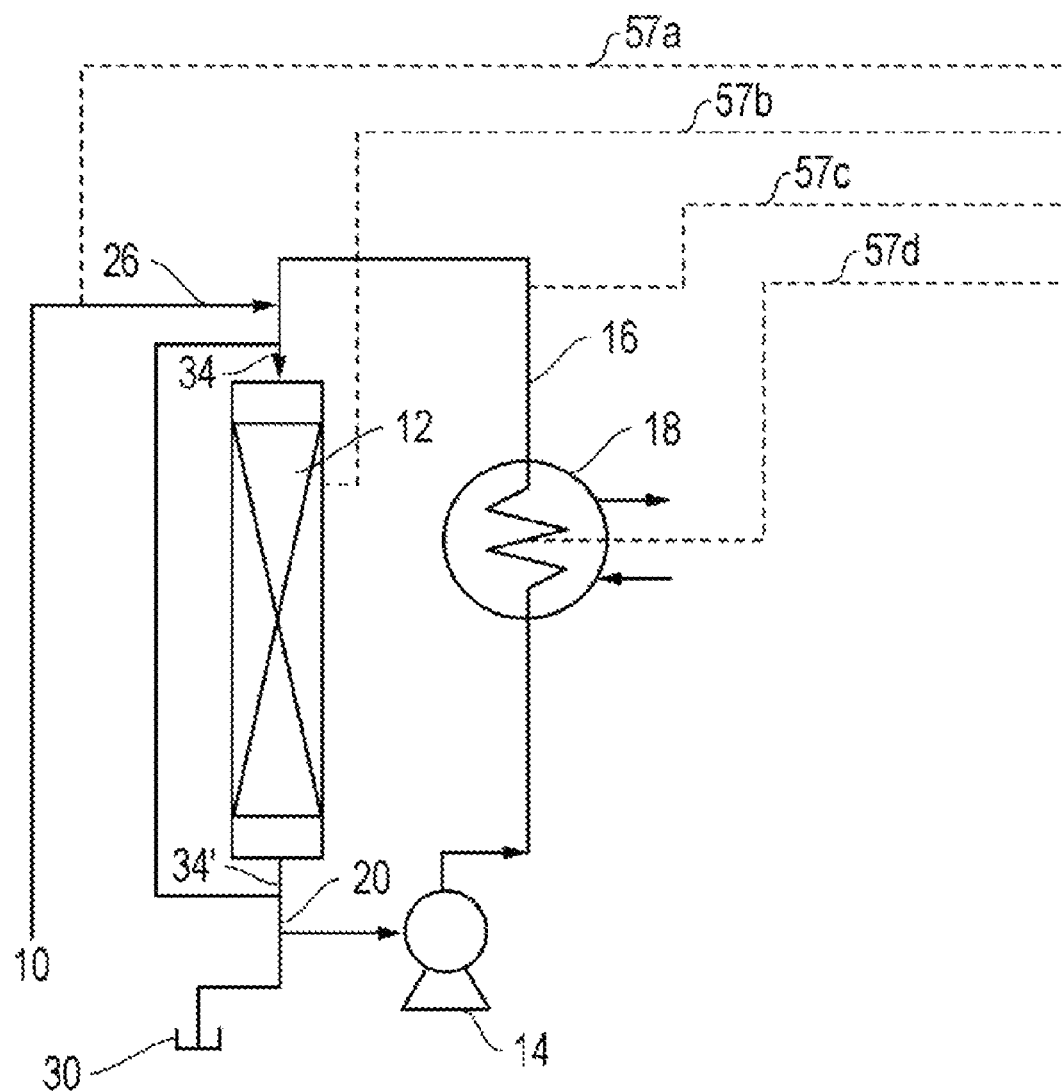
FIG. 1 is a schematic diagram of an adaptation of the reactor system used in Example 18.

The present application provides catalysts comprising a combination of oxidized metals. The catalysts are useful to cleave phenylalkyl hydroperoxides, even at relatively high concentrations.

Cleavage of phenylalkyl hydroperoxides using catalysts comprising a combination of metals produces a number of advantages when compared to the use of dilute sulfuric acid to cleave the phenylalkyl hydroperoxides. Advantages include, but are not necessarily limited to: minimizing handling of hazardous liquid acids; eliminating a neutralization step; reducing the water content of the neutralized reaction solution; reducing the energy cost of boiling additional water; removing corrosive salts from the reaction mixture; increasing the yield of desired products; minimizing impurities; reducing equipment costs required to run the process; reducing operating costs; and, minimizing unwanted hydroxyketones and ketone condensation products.

Phenylalkyl hydroperoxides which may be cleaved using the catalysts have the following general structure:

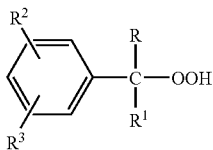

wherein

R and $R^1$ independently are selected from the group consisting of hydrogen and alkylene groups having 1 or more carbon atoms, preferably 5 carbon atoms or less, wherein R and $R^1$ optionally may be linked together to form a ring structure; and $R^2$ and $R^3$ independently are selected from the group consisting of hydrogen, hydroxyl groups, and alkyl groups having from about 1 to 4 carbon atoms. In one embodiment, $R^2$ and $R^3$ are selected from the group consisting of hydrogen and methyl groups.

In preferred embodiments, R and $R^1$ independently are selected from the group consisting of methyl groups and ethyl groups. In a cumene process, the phenylalkyl hydroperoxide is cumyl hydroperoxide. In a sec-butyl benzene process, the phenylalkyl hydroperoxide is sec-butylbenzene hydroperoxide. In a cyclohexylbenzene hydroperoxide process, the hydroperoxide is cyclohexylbenzene hydroperoxide. In one embodiment, the hydroperoxide is a combination of cumyl hydroperoxide and sec-butylbenzene hydroperoxide.

The choice of $R^2$ and $R^3$ will depend upon the desired product. During oxidation of phenylalkanes, $R^2$ and $R^3$ groups having 2 carbon atoms or more would be expected to oxidize. Depending upon the oxidation conditions, $R^2$ and $R^3$ groups having 2 carbon atoms or more could attain various levels of oxidation. Upon substantially complete oxidation, $R^2$ and $R^3$ groups having 2 carbon atoms or more could oxidize to the corresponding hydroperoxides and be cleaved to hydroxybenzene and the corresponding ketones. Under differing oxidation conditions, $R^2$ and $R^3$ groups having 2 carbon atoms or more could oxidize to a hydroxybenzene group and acetaldehyde. Oxidation is less likely to occur where the substituent is a methyl group. In one embodiment, $R^2$ and $R^3$ are hydrogen.

Cleavage of the phenylalkyl hydroperoxides produces a cleavage product comprising ketones and hydroxybenzenes. The cleavage product also includes byproducts, including but not necessarily limited to phenylalkenes, phenylalkyl ketones, di(phenylalkyl)peroxides, and phenylalkyl alcohols. Depending upon the conditions, the cleavage product also may comprise phenylalkene-derived heavy ends. Examples of phenylalkene-derived heavy ends include dimers of phenylalkene and/or the reaction product between phenylalkene and phenol.

Ketones in the cleavage product generally have the following structure:

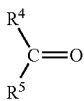

wherein $R^4$ and $R^5$ are alkyl groups having 1 or more carbon atoms, preferably having 6 carbon atoms or less. $R^4$ and $R^5$ also may be joined to form a ring. In one embodiment, $R^4$ and $R^5$ are joined to form cyclohexanone.

Hydroxybenzenes in the cleavage product generally have the following structure:

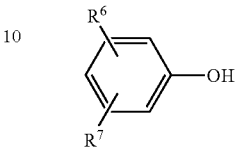

wherein $R^6$ and $R^7$ independently are selected from the group consisting of hydrogen, hydroxyl groups, and methyl groups.

Phenylalkenes which may be byproducts in the cleavage product have the following general structure:

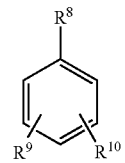

wherein $R^8$ is an alkenyl group comprising one or more unsaturated carbon-carbon bond and having 2 carbon atoms or more, preferably having 6 carbon atoms or less, depending upon the phenylalkyl hydroperoxides cleaved; and, $R^9$ and $R^{10}$ independently are selected from the group consisting of hydrogen, hydroxyl groups, and methyl groups. In one embodiment, $R^9$ and $R^{10}$ independently are selected from the group consisting of hydrogen and methyl groups.

Where the process is a cumene process, $R^9$ and $R^{10}$ are hydrogens, and the phenylalkene is α-methylstyrene (AMS), which has the following general structure:

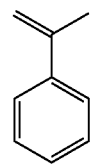

Phenylalkyl ketones present as byproduct in the cleavage product generally have the following structure:

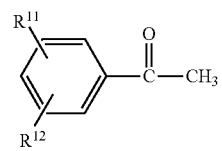

wherein $R^{11}$ and $R^{12}$ independently are selected from the group consisting of hydrogen, hydroxyl groups, and methyl groups.

Where the process is a cumene process, the phenylalkyl ketone generally is acetophenone, which has the following structure:

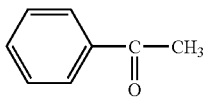

Where present, the di(phenylalkyl)peroxide byproducts in the cleavage product generally have the following structure:

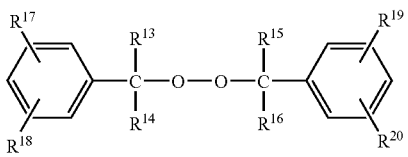

wherein $R^{13}$, $R^{14}$, $R^{15}$, and $R^{16}$ are the same or different, and are selected from the group consisting of alkyl groups having 1 carbon atom or more, preferably having 5 carbon atoms or less, depending upon the phenylalkyl hydroperoxides, wherein a combination selected from the group consisting of (a) $R^{13}$ and $R^{14}$ and (b) $R^{15}$ and $R^{16}$ optionally may be linked together to form a ring structure; and, $R^{17}$, $R^{18}$, $R^{19}$ and $R^{20}$ independently are selected from the group consisting of hydrogen, hydroxyl groups, and methyl groups.

In a cumene process, $R^{17}$, $R^{18}$, $R^{19}$, and $R^{20}$ are hydrogen and the di(phenylalkyl)peroxide generally is dicumyl peroxide, which has the following general structure:

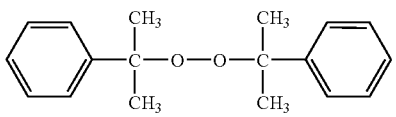

The phenylalkyl alcohols in the cleavage product generally have the following structure:

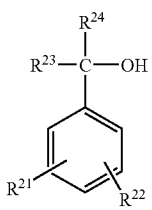

wherein $R^{21}$ and $R^{22}$ independently are selected from the group consisting of hydrogen, hydroxyl groups, and methyl groups; and, $R^{23}$ and $R^{24}$ independently are selected from the group consisting of alkyl groups having 1 to 6 carbon atoms, preferably 1 to 2 carbon atoms, depending upon the phenylalkyl hydroperoxides cleaved.

Where the process is a cumene process, $R^{21}$ and $R^{22}$ are hydrogen and the phenylalkyl alcohol is dimethylbenzyl alcohol (DMBA), which has the following general structure:

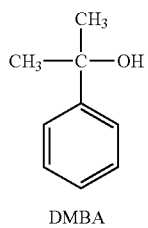

DMBA

Where the process is a sec-butyl benzene process, $R^{21}$ and $R^{22}$ also are hydrogen, and the phenylalkyl alcohol is ethylmethyl benzyl alcohol (EMBA), which has the following general structure:

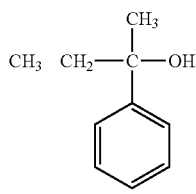

EMBA

The Catalyst and its Preparation

The cleavage of the phenylalkyl hydroperoxides occurs in the presence of a catalyst comprising a combination of oxidized metals. As used herein the plural form of a word, such as "hydroperoxides," generally may be interpreted as singular or plural.

Suitable catalysts comprise a combination of oxidized metals wherein the metals comprise: (i) a first metal selected from the group consisting of tin, iron, zinc, bismuth, cerium, and combinations thereof, and (ii) a second metal selected from the group consisting of zirconium, antimony, titanium, tungsten, and combinations thereof. In a preferred embodiment, (i) the first metal is selected from the group consisting of tin, zinc, cerium, and combinations thereof, and (ii) the second metal is selected from the group consisting of tungsten, zirconium, and combinations thereof. In preferred embodiments, the catalysts comprise oxidized forms of a combination of metals selected from the group consisting of: tungsten and tin; tungsten and iron; tungsten and cerium; tungsten and bismuth; tungsten and zinc; zirconium and tin; and, antimony and tin. In one embodiment, the catalyst comprises oxidized tin and oxidized zirconium. In one embodiment, the catalyst comprises about 10 wt. % zirconium and about 5 wt. % tin (IV), based on the total weight of the catalyst.

Some oxidized metals tend to slowly dissolve in the cleavage reaction mixture. Other oxidized metals have less of a tendency to dissolve in the cleavage reaction mixture. Catalyst comprising oxidized tin and oxidized zirconium has the advantage that it has less of a tendency to dissolve in the cleavage reaction mixture.

The catalyst may consist of 100 wt. % oxidized metal. Where the catalyst is 100% oxidized metal, the catalyst may be made according to the methods described in U.S. Pat. No. 6,169,215, incorporated herein by reference. Generally, the method involves calcining a source of the first metal with a source of a second metal at a temperature of 400° C. or more.

The use of a support is preferred, particularly where the use of a support reduces the cost of the catalyst. A variety of supports are useful. By way of example, suitable supports include but are not necessary limited to silica, alumina, silica-alumina, titania, zirconia, zeolites, and acidic clays. Where the support comprises one or more zeolitic material(s), suitable zeolites include, but are not necessarily limited to zeolite beta and zeolites having a Constraint Index of from 1 to 12. Examples of suitable acidic clays include, but are not necessarily limited to kaolinite, attapulgite, montmorillonite, and cloisite clays.

Supported oxidized metals may be made using a variety of methods and may comprise a variety of structures. Suitable methods of preparation include, but are not necessarily limited to impregnation, coimpregnation, including single or multiple impregnations, coprecipitation, physical admixture or any other suitable method. The method employed will depend on the solubility of the source of metal and the conditions required to convert the source to the metal. In a preferred embodiment, supported catalysts comprising a combination of oxidized metals are prepared by precipitating sources of a combination of metals onto the support, separately or in the same procedure. Suitable sources of metals for precipitation include, but are not necessarily limited to metal nitrates, metal chlorides, metal acetates, metal sulfates, and metal ammonium salts, etc. For example, suitable water soluble sources of zirconium include, but are not necessarily limited to zirconyl chloride, zirconyl nitrate, zirconium tetraacetate, and combinations thereof.

Where the source of metal is a metal chloride, it is convenient to hydrolyze the metal chloride in the presence of acid or base before calcination of the impregnated support. Substantially any acid or base effective to hydrolyze the metal chloride may be used. In the examples, ammonium hydroxide was used as the base. Dilute nitric acid was used as the acid.

After deposition of a source of one or more metals onto the support, the material is dried and calcined at a temperature of 400° C. or more, preferably at a temperature of from 450° C. to 1200° C., more preferably at a temperature of 500° C. or more, typically at a temperature from 500° C. to 1000° C. The calcination continues, for example, for a period of from about 2 hours to about 30 hours. In a preferred embodiment, calcination occurs after deposition of a combination of metals.

Preferably, the catalyst comprises about 40 wt. % or less, suitably about 5 wt. % or more, of a combination of metals based on the total weight of the catalyst. In one embodiment, the catalyst comprises from about 2 wt. % to about 20 wt. % of each of two metals, based on the total weight of the catalyst, as measured by elemental analysis.

After calcination, the catalyst comprises a combination of a first amount of a first oxidized metal and a second amount of a second oxidized metal. The combination has sufficient acidity to cleave the phenylalkyl hydroperoxide. In one embodiment, the acidity of the combination is greater than that of a mixture formed by separately oxidizing the first metal and the second metal and subsequently mixing the first amount of the oxidized first metal with the second amount of the oxidized second metal.

Without wishing to be bound by theory, it is believed that the acidity of the combination of oxidized metals is increased by calcining both metals together at the same time. Again, without limiting the application to a particular structure, it has been theorized that superacids are formed when sulfates and possibly tungstates react with hydroxides or oxides of certain metals. It is believed that these superacids have the structure of a bidentate sulfate or tungstate ion coordinated to the metal. However, the particular structure of the catalytically active site has not been confirmed.

The Cleavage Process

The method of using the catalyst to cleave phenylalkyl hydroperoxide may be batchwise or continuous. In one embodiment, the process is continuous. As used herein, the word "continuous" or "continuously" is intended to include processes which are continuous, but which may be subject to interruptions for various practical reasons. Examples of such interruptions include maintenance of equipment, cleaning, updating of equipment, and the like. By way of example only, and without limiting the process to a specific amount of downtime, the downtime in a "continuous" process generally is about 5% or less, based on total available operating time.

The cleavage feed comprises a phenylalkyl hydroperoxide feed comprising one or more phenylalkyl hydroperoxides. By way of example only, the cleavage feed comprises from about 0.5 wt. % to about 3 wt. % water, based on the total weight of the cleavage feed.

The cleavage feed may have substantially any concentration of phenylalkyl hydroperoxides. However, in order to avoid the need to handle large quantities of diluent, the phenylalkyl hydroperoxide feed suitably comprises 70 wt. % or more phenylalkyl hydroperoxides. In one embodiment, the phenylalkyl hydroperoxide feed comprises more than 70 wt. % phenylalkyl hydroperoxides, based on the total weight of the cleavage feed. In another embodiment, the phenylalkyl hydroperoxide feed comprises from about 70 wt. % to about 90 wt. % phenylalkyl hydroperoxides. In yet another embodiment, the phenylalkyl hydroperoxide feed comprises 80 wt. % or more phenylalkyl hydroperoxide. In one embodiment, the phenylalkyl hydroperoxide feed comprises from about 80 wt. % to about 88 wt. % phenylalkyl hydroperoxide, based on the total weight of the cleavage feed.

In one embodiment, the cleavage reaction mixture is subjected to cleavage conditions in the presence of catalyst. The reactor may be packed with catalyst, or the catalyst may be fed to the reactor. In one embodiment, the catalyst is fed to the reactor with the cleavage feed.

In one embodiment of a continuous process, the phenylalkyl hydroperoxide feed rate is 1 gram or less of phenylalkyl hydroperoxide feed per gram of catalyst per hour. Where the reaction is continuous, the cleavage conditions comprise a liquid hourly space velocity (LHSV) of from about $0.1\ hr^{-1}$ to $100\ hr^{-1}$, preferably from about $20\ hr^{-1}$ to about $60\ hr^{-4}$, based on the concentration of phenylalkyl hydroperoxide. Where the reaction is batchwise, the cleavage conditions comprise a residence time of from about 1 minute to about 360 minutes, preferably from about 1 minute to about 180 minutes.

An additional ketone feed is not required. However, feeding a ketone feed to the cleavage reactor will aid in reducing the production of non-recoverable by-products, for example, phenylalkyl alcohols and phenylalkene dimers. In one embodiment, the cleavage feed also comprises ketone feed.

Where a ketone feed is provided, the ketone feed rate is from about 0.1 wt. % to about 10 wt. % based on the phenylalkyl hydroperoxide feed rate. In one embodiment, the ketone feed rate is about 10 wt. % based on the phenylalkyl hydroperoxide feed rate. In other words, where the phenylalkyl hydroperoxide feed rate is 1 gram or less of phenylalkyl hydroperoxide feed per gram of catalyst per hour, the ketone feed rate is from about 0.001 gram to about 0.1 gram or less of ketone feed per gram of catalyst per hour. In one embodiment, the ketone feed rate is about 0.1 gram of ketone feed per gram of catalyst per hour.

The one or more ketones in the ketone feed suitably are the same as the ketones produced by cleaving the phenylalkyl hydroperoxides. In one embodiment, the ketone feed is recycled from a cleavage product separation zone.

The cleavage conditions comprise subjecting the cleavage reaction mixture to a temperature of 90° C. or less, preferably about 40° C. or more, more preferably about 50° C. or more, more preferably from about 50° C. to about 70° C. The temperature may be maintained in any suitable manner.

The cleavage conditions also comprise subjecting the cleavage reaction mixture to a pressure of from about 15 kPa to 8000 kPa, more preferably from atmospheric pressure to from about 55 kPa to 7000 kPa. In one embodiment, the pressure is atmospheric pressure (typically about 100 kPa).

A portion of the cleavage product preferably is recycled to the cleavage reactor. Preferably, the ratio of recycled cleavage product to cleavage feed is from about 10:1 to about 100:1 on a weight basis, and more preferably from about 20:1 to 40:1 on a weight basis. In one embodiment, from about 10 wt. % to about 40% wt. of the cleavage product is recycled to the cleavage reactor. In one embodiment, from about 20% wt. to about 30% wt. of the cleavage product is recycled to the cleavage reactor. More preferably about 20% wt. of the cleavage product is recycled to the cleavage reactor.

A variety of reactor types are suitable, including, for example, packed bed reactors, fluidized bed reactors, slurry reactors, continuous stirred tank reactors (CSTR's), reflux cooled (boiling) reactors, reactive distillation columns, plug-flow reactors ("PPR's"), and plug-flow reactors with recycle (PFRR's).

Optimum cleavage conditions may be established by adjusting various parameters. The conditions will vary with the number of reactors and the type of reactor(s) used. For example, where the reactor is a packed bed reactor, the temperature and catalyst bed size may be varied to achieve a maximum yield of phenol or an optimum slate of phenol and desired byproducts, including di(phenylalkyl)peroxide and/or α-methyl styrene (AMS). Persons of ordinary skill in the art will be able to establish optimum conditions using a particular reactor system, catalyst, and feed.

The selectivity of the process to various components may vary depending upon a number of factors, including whether the process is batchwise or continuous, and the intended use of the cleavage reaction mixture.

In one embodiment of the present invention, in which the cleavage product is designed to feed to a second stage in which di(phenylalkyl)peroxide is cleaved, the relatively mild cleavage conditions increase the concentration of di(phenylalkyl)peroxide in the cleavage product relative to the amount of di(phenylalkyl)peroxide in the cleavage feed. In a preferred embodiment, the cleavage product comprises from about 1 wt. % to about 5 wt. % di(phenylalkyl)peroxide.

Another variable is the selectivity of the cleavage to α-methyl styrene (AMS). The desired selectivity to AMS will vary depending upon the intended use of the cleavage product. If the process is conducted in a single stage, then the selectivity to AMS should be comparable to or better than the selectivity of commercial cumene processes using dilute sulfuric acid as catalyst.

In a commercial cumene process using dilute sulfuric acid as catalyst, acceptable selectivity to AMS is about 0.55 or more, based on the components in the cleavage feed (cumene hydroperoxide) that can theoretically produce AMS. Advantageous commercial cumene processes using dilute sulfuric acid can produce selectivity to α-methyl styrene of about 0.70 or more, based on the components in the cleavage feed that can theoretically produce AMS.

Where the intended use of the cleavage product is as a feed to a second stage in which di(phenylalkyl)peroxide is cleaved, it is possible to produce a selectivity to AMS of about 0.70 or more, based on the components in the feed to the second stage of the reactor that theoretically can produce AMS and the content of AMS in the second stage product. Preferably, the selectivity to AMS after the second stage is 0.73 or more. In an advantageous embodiment, the selectivity to AMS after the second stage is 0.80 or more.

One suitable system for continuous operation using the catalysts of the present application is an adaptation of the bench scale system used in Example 18 (FIG. 1). Referring to FIG. 1, the cleavage reactor 12 is a column reactor packed with catalyst. The cleavage feed 10 is added to a recycle loop 16. The temperature in the cleavage reactor 12 is controlled by any suitable means. In the illustrated embodiment, the temperature is controlled by regulating the steam to the heat exchanger 18, as well as by the feed rate and the recycle rate.

In commercial use, ketone feed is introduced to the cleavage reactor at any suitable location. In one embodiment, a ketone feed 57a is introduced into the cleavage feed 10. In another embodiment, ketone feed 57b is introduced directly into the cleavage reactor 12. In another embodiment, ketone feed 57c is introduced into recycle loop 16. In yet another embodiment, ketone feed 57d is introduced via the heat exchanger 18 by a feed line which may be introduced into the condensing column, or the column containing the cleavage reaction mixture.

Figure 2:
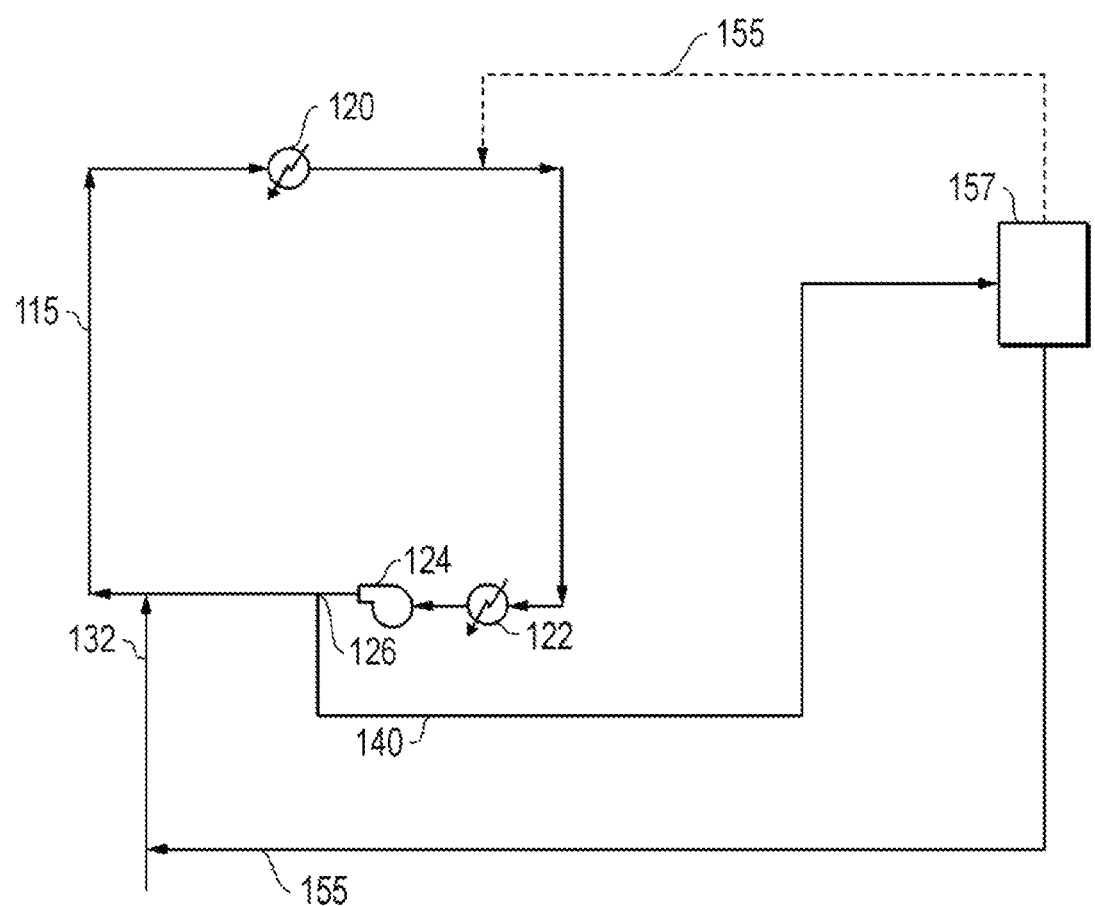
FIG. 2 is a schematic diagram of another reactor system suitable for practicing the method described herein.

FIG. 2 illustrates another embodiment of a reactor system suitable for practicing the present method. In this embodiment the cleavage reactor 115 is a pipeline loop reactor. The reactor 115 comprises one or more heat exchangers 120, 122 at appropriate locations to provide cooling sufficient to maintain the cleavage reaction mixture at the cleavage reaction temperature. A pump 124 is installed in the pipeline loop to provide for recirculation of a recycle flow of the cleavage reaction mixture, including catalyst, through the cleavage reactor 115. The cleavage reaction product 140, is withdrawn from the pipeline loop reactor at a withdrawal point 126. Ketone feed 155 is fed into the cleavage reactor at any suitable location. In one embodiment, a ketone feed 155 is fed to the cleavage reactor feed 132. In another embodiment, indicated in dotted lines, a ketone feed 155 is fed directly to the cleavage reactor 115. Alternately, the ketone feed may be introduced via the heat exchanger 120 and/or 122 by a feed line introduced into the condensing column, or the column containing the cleavage reaction mixture. In one embodiment, ketone feed 155 is recycled from a cleavage product separation zone 157.

The invention will be more clearly understood with reference to the following Examples, which are provided by way of example only.

EXAMPLES

Synthesis of Catalysts

Examples 1-8 illustrate the preparation of catalysts according to the invention comprising a combination of oxidized metals.

Example 1

20 grams of 99 wt. % silica obtained from CRI International (Houston, Tex., USA) ("CRI") was impregnated with a solution containing 8.8 grams of tin tetrachloride in 15 ml of methylene chloride. The solution was mixed with the silica for 20 minutes. The solvent was evaporated and the resultant solid was immersed in 4 molar, 14 wt. % ammonium hydroxide solution. The mixture was allowed to stand overnight. The mixture was washed with deionized water until neutral. The solid was dried in a vacuum oven at 80-120° C. overnight. The dried, tin-impregnated silica was impregnated with a solution containing 1.35 grams of ammonium metatungstate in 20 grams of deionized water. The resulting metal impregnated silica was dried at 80-120° C. and calcined at 1000° C. in flowing air for 3 hours. The catalyst contains approximately 16 wt. % tin and approximately 3.8 wt. % tungsten by the mode of synthesis.

Example 2

7.6 grams of $Ce(NO_3)_3.6H_2O$ were dissolved with stirring in 20 grams of deionized water. 20 grams of silica extrudate obtained from CRI was impregnated with the cerium solution and aged at room temperature overnight. The Ce-impregnated silica was then dried and the solvent evaporated in an oven at 150° C. for 3 hours. The dried Ce-impregnated catalyst was impregnated with a solution containing 1.65 grams ammonium metatungstate in 20 ml of deionized water and aged for 1 hour. The resulting impregnated catalyst was dried and the solvent evaporated in the oven at 150° C. for 1 hour and calcined at 1000° C. for 3 hours. The catalyst contains approximately 10 wt. % cerium and approximately 5 wt. % tungsten by the mode of synthesis.

Example 3

146.05 grams of $Zn(O_2CCH_3)_2.2H_2O$ were dissolved with stirring in 28 grams of deionized water. 30 grams of silica extrudate obtained from CRI was impregnated with the solution and allowed to age for 1 hour. The Zn-impregnated silica was dried and the solvent evaporated in an oven at 150° C. for 3 hours. The dried Zn-impregnated silica was impregnated with a solution containing 5.06 grams of ammonium metatungstate in 30 grams of deionized water. The catalyst was aged for 1 hour and dried and the solvent evaporated in the oven at 150° C. for 3 hours and calcined at 800° C. for 3 hours. The catalyst contains approximately 48.9 wt. % zinc and approximately 4.3 wt. % tungsten by the mode of synthesis.

Example 4

1.91 grams of $Bi(NO_3)_3.5H_2O$ were dissolved with stirring in 29 g of distilled water. 30 grams of silica extrudate obtained from CRI was impregnated with the solution and allowed to age for 1 hour. The impregnated silica was dried and the solvent evaporated in an oven at 150° C. for 3 hours. The dried impregnated catalyst was impregnated with a solution of 2.0 grams ammonium metatungstate in 28 grams of deionized water. The resulting impregnated catalyst was allowed to age for 1 hour and was dried and the solvent evaporated in the oven at 150° C. for 3 hours and then calcined at 700° C. for 3 hours. The catalyst contains 2.5 wt. % bismuth and 4.6 wt. % tungsten by the mode of synthesis.

Example 5

146.05 grams of $Zn(O_2CCH_3)_2.2H_2O$ were dissolved with stirring in 28 grams of deionized water. 30 grams of silica extrudate obtained from CRI was impregnated with the solution and allowed to age for 1 hour. The Zn-impregnated silica was dried and the solvent evaporated_in an oven at 150° C. for 3 hours. The dried Zn-impregnated silica was impregnated with a solution containing 5.06 grams of ammonium metatungstate in 30 grams of deionized water. The catalyst was aged for 1 hour and dried and the solvent evaporated in the oven at 150° C. for 3 hours and calcined at 800° C. for 3 hours. The catalyst contains 49 wt. % zinc and 4.3 wt. % tungsten by the mode of synthesis.

Example 6

150 grams of 99% silica from CRI was impregnated with 154 ml of an aqueous solution containing 28.0 g of tin tetrachloride and 66.5 g zirconyl chloride octahydrate. The silica was mixed for 5 minutes and the mixture aged for 1 hour with occasional mixing. The silica impregnated with tin and zirconium was transferred to a container and covered with 4 molar ammonium hydroxide solution and left at room temperature for 3 hours with occasional mixing. The ammonia was decanted and the silica was washed with deionized water until the pH was constant. The tin and zirconium impregnated silica was dried and the solvent evaporated at 150° C. for 2 hours and then calcined at 1000° C. in flowing air for 1 hour. The catalyst contains 6.6% tin and 9.8% zirconium by the mode of synthesis.

Example 7

20.25 grams of silica extrudate obtained from CRI was impregnated with 21 ml of an isopropanol solution containing 3.12 grams of $SbCl_5$ and 2.76 grams of $SnCl_4$. The silica was mixed for 5 minutes and the mixture was aged for 1 hour with occasional mixing. The Sb and Sn impregnated silica was transferred to a container and covered with 7% nitric acid solution. The mixture was left at room temperature for 3 hours with occasional mixing. The acid was decanted and the silica was washed with deionized water until the pH was constant. The solid was dried at 120° C. for 15 hours and then calcined at 800° C. in flowing air for 3 hours. The catalyst comprises 5.4 wt % Sb and 5.9 wt. % Sn by the mode of synthesis.

Example 8

26 grams of $Fe(NO_3)_3.9H_2O$ were dissolved with stirring in 24 grams of deionized water. 25 grams of silica extrudate obtained from CRI was impregnated with the solution and allowed to age for 1 hour. The Fe-impregnated silica was dried and the solvent evaporated_in an oven at 150° C. for 3 hours. The resultant solid was immersed in 4 molar, 14 wt. % ammonium hydroxide solution. The mixture was allowed to stand for 30 minutes. The mixture was washed with deionized water until neutral, and then dried at 150° C. for 3 hours. The dried Fe-impregnated silica was then impregnated with a solution containing 2.9 grams of ammonium metatungstate in 24 ml of deionized water. The catalyst was aged for 1 hour at room temperature (approx. 20° C.) and solvent evaporated in the oven at 150° C. for 3 hours and calcined at 700° C. for 2 hours. The catalyst contains 8.4 wt. % iron and 5.1 wt. % tungsten by the mode of synthesis.

Cleavage Reaction

In the following examples, the cleavage reaction was performed under dilute cumene hydroperoxide conditions using catalysts according to the present invention.

Example 9

To a 250-ml round bottom flask fitted with a condenser, stirrer, dropping funnel, heating mantle and temperature regulator for temperature control, was charged a mixture of 100.0 g of acetone and 5.00 g of the catalyst of Example 1. The mixture was heated to reflux (57° C.) with stirring, and 50.0 g of a solution containing 35.1 wt. % cumene hydroperoxide, 35.1 wt. % sec-butyl benzene hydroperoxide, 1.4 wt. % cumene, 18.5 wt. % sec-butylbenzene, 3.8 wt. % acetophenone, 4.8 wt. % dimethylbenzyl alcohol and 1.2 wt. % 2-phenyl-2-butanol was added dropwise at an approximate rate of 2 g/min. Following addition of the hydroperoxide solution, small samples (~0.2 ml) of the cleavage solution were withdrawn at regular intervals, filtered, and analyzed by HPLC for cumene hydroperoxide, sec-butylbenzene hydroperoxide, phenol, dimethylbenzyl alcohol, 2-phenyl-2-butanol, cumylphenol, 2-phenyl-2-butylphenol, α-methylstyrene, acetophenone, dimers of α-methylstyrene and 2-phenyl-2-butene, dicumyl peroxide, cumene, and sec-butylbenzene.

The following Table shows the composition (wt. %) of the cleavage solution at 0 minutes, 15 minutes, 30 minutes, 60 minutes, and 120 minutes after completion of the addition of the cumene hydroperoxide/sec-butyl benzene hydroperoxide solution:

| SnO$_2$/WO$_3$ | 0 min. | 15 min. | 30 min. | 60 min. | 120 min. |
|---|---|---|---|---|---|
| Phenol | 10.3 | 13.5 | 14.6 | 13.9 | 14.5 |
| acetophenone | 1.38 | 1.42 | 1.46 | 1.37 | 1.42 |
| dimethylbenzyl alcohol | 1.16 | 1 | 0.92 | 0.72 | 0.57 |
| cumene hydroperoxide | 2.7 | 0.49 | 0.0 | 0.0 | 0.0 |
| 2-phenyl-2-butanol | 1.21 | 0.5 | 0.5 | 0.42 | 0.37 |
| sec-butyl benzene hydroperoxide | 2.74 | 0.43 | 0.0 | 0.0 | 0.0 |
| Cumyl phenol | 0.0 | 0.0 | 0.0 | 0.0 | 0.0 |
| α-methylstyrene | 0.07 | 0.12 | 0.18 | 0.28 | 0.45 |
| 2-phenyl-2-butyl-phenol | 0.0 | 0.0 | 0.0 | 0.0 | 0.0 |
| cumene | 0.55 | 0.55 | 0.57 | 0.54 | 0.56 |
| sec-butylbenzene | 6.65 | 6.76 | 6.96 | 6.53 | 6.76 |
| dicumylperoxide | 0.27 | 0.37 | 0.4 | 0.38 | 0.39 |
| dimers of α-methylstyrene | 0.05 | 0.29 | 0.01 | 0.22 | 0.03 |
| % cumene hydroperoxide conversion | 76.8 | 96.1 | 100 | 100 | 100 |

The results show 100% conversion of cumene hydroperoxide and sec-butyl benzene hydroperoxide. The product contained the following wt. % of the following components, based on the total weight of the cleavage product: less than 0.5 wt. % α-methylstyrene (and dimers); less than 1.5 wt. % acetophenone; less than 0.6 wt. % DMBA; less than 0.4 wt. % 2-phenyl-2-butanol; and less than 0.4 wt. % unconverted dicumylperoxide.

Example 10

To a 250-ml round bottom flask fitted with a condenser, stirrer and dropping funnel, heating mantle and temperature regulator for temperature control, was charged a mixture of 100.0 g of acetone and 5.00 g of the catalyst of Example 1. The mixture was heated to reflux (57° C.) with stirring, and 50.0 g of 86% cumene hydroperoxide (analyzed as 86.1 wt. % cumene hydroperoxide, 10.5 wt. % cumene, 3.4 wt. % dimethylbenzyl alcohol, 0.4 wt. % acetophenone) was added dropwise at an approximate rate of 2 g/min. Following addition of the cumene hydroperoxide solution, small samples (~0.2 ml) of the cleavage solution were withdrawn at regular intervals, filtered, and analyzed by HPLC for phenol, cumene hydroperoxide, dimethylbenzyl alcohol, α-methylstyrene, and dimers of α-methylstyrene, dicumyl peroxide, cumylphenol and acetophenone.

The following Table shows the composition (wt. %) of the cleavage solution at 0 minutes, 15 minutes, 30 minutes, and 60 minutes after the completion of addition of the cumene hydroperoxide. The results show 100% conversion of cumene hydroperoxide. The product contained the following components in wt. %, based on the total weight of the cleavage product: less than 0.2 wt. % acetophenone; less than 0.2 wt. % DMBA; less than 0.5 wt. % cumylphenol; less than 1 wt. % α-methylstyrene.

| SnO$_2$/WO$_3$ | 0 min. | 15 min. | 30 min. | 60 min. |
|---|---|---|---|---|
| phenol | 16.3 | 16.3 | 16.3 | 16.3 |
| acetophenone | 0.15 | 0.15 | 0.16 | 0.16 |
| dimethylbenzyl alcohol | 0.49 | 0.29 | 0.21 | 0.11 |
| cumene Hydroperoxide | — | — | — | — |
| cumylphenol | 0.01 | 0.02 | 0.03 | 0.03 |
| α-methylstyrene | 0.35 | 0.52 | 0.64 | 0.76 |
| cumene | 4.13 | 4.02 | 4.16 | 4.20 |
| dicumylperoxide | 0.7 | 0.6 | 0.6 | 0.5 |
| α-methylstyrene dimers | 0.0 | 0.0 | 0.0 | 0.0 |
| % cumene hydro-peroxide conversion | 100.0 | 100.0 | 100.0 | 100.0 |

Example 11

To a 250-ml round bottom flask fitted with a condenser, stirrer, dropping funnel, heating mantle and temperature regulator for temperature control, was charged a mixture of 100.0 g of acetone and 5.00 g of the catalyst of Example 1. The mixture was heated to reflux (57° C.) with stirring, and 50.0 g of a solution containing 35.1 wt. % cumene hydroperoxide, 35.1 wt. % sec-butyl benzene hydroperoxide, 1.4 wt. % cumene, 18.5 wt. % sec-butylbenzene, 3.8 wt. % acetophenone, 4.8 wt. % dimethylbenzyl alcohol and 1.2 wt. % 2-phenyl-2-butanol was added dropwise at an approximate rate of 2 g/min. Following addition of the hydroperoxide solution, small samples (~0.2 ml) of the cleavage solution were withdrawn at regular intervals, filtered, and analyzed by HPLC for cumene hydroperoxide, sec-butylbenzene hydroperoxide, phenol, dimethylbenzyl alcohol, 2-phenyl-2-butanol, cumylphenol, 2-phenyl-2-butylphenol, α-methylstyrene, acetophenone, dimers of α-methylstyrene and 2-phenyl-2-butene, dicumyl peroxide, cumene, and sec-butylbenzene.

The following Table shows the composition (wt. %) of the cleavage solution at 0 minutes, 15 minutes, 30 minutes, 60 minutes, and 120 minutes after completion of the addition of the cumene hydroperoxide/sec-butyl benzene hydroperoxide solution. The results show 100% conversion of cumene hydroperoxide and sec-butyl benzene hydroperoxide. The product contained the following components in wt. %, based on the total weight of the cleavage product: less than 0.5 wt. % α-methylstyrene (and dimers); less than 1.5 wt. % acetophenone; less than 0.6 wt. % DMBA; less than 0.4 wt. % 2-phenyl-2-butanol; and less than 0.4 wt. % unconverted dicumylperoxide.

| SnO$_2$/WO$_3$ | 0 min. | 15 min. | 30 min. | 60 min. | 120 min. |
|---|---|---|---|---|---|
| Phenol | 10.3 | 13.5 | 14.6 | 13.9 | 14.5 |
| Acetophenone | 1.38 | 1.42 | 1.46 | 1.37 | 1.42 |

-continued

| SnO$_2$/WO$_3$ | 0 min. | 15 min. | 30 min. | 60 min. | 120 min. |
|---|---|---|---|---|---|
| dimethylbenzyl alcohol | 1.16 | 1 | 0.92 | 0.72 | 0.57 |
| cumene hydroperoxide | 2.7 | 0.49 | 0.0 | 0.0 | 0.0 |
| 2-phenyl-2-butanol | 1.21 | 0.5 | 0.5 | 0.42 | 0.37 |
| sec-butyl benzene hydroperoxide | 2.74 | 0.43 | 0.0 | 0.0 | 0.0 |
| Cumyl phenol | 0.0 | 0.0 | 0.0 | 0.0 | 0.0 |
| α-methylstyrene | 0.07 | 0.12 | 0.18 | 0.28 | 0.45 |
| 2-phenyl-2-butyl-phenol | 0.0 | 0.0 | 0.0 | 0.0 | 0.0 |
| Cumene | 0.55 | 0.55 | 0.57 | 0.54 | 0.56 |
| sec-butylbenzene | 6.65 | 6.76 | 6.96 | 6.53 | 6.76 |
| Dicumylperoxide | 0.27 | 0.37 | 0.4 | 0.38 | 0.39 |
| dimers of α-methylstyrene | 0.05 | 0.29 | 0.01 | 0.22 | 0.03 |
| % cumene hydroperoxide conversion | 76.8 | 96.1 | 100 | 100 | 100 |

Example 12

To a 250-ml round bottom flask fitted with a condenser, stirrer, dropping funnel, heating mantle and temperature regulator for temperature control, was charged a mixture of 100.0 g of acetone and 5.00 g of the catalyst of Example 8. The mixture was heated to reflux (57° C.) with stirring, and 50.0 g of 86% cumene hydroperoxide solution (analyzed as 86.1 wt. % cumene hydroperoxide, 10.5 wt. % cumene, 3.2 wt. % dimethylbenzyl alcohol, 0.4 wt. % acetophenone) was added dropwise at an approximate rate of 2 g/min. Following addition of the cumene hydroperoxide solution, small samples (~0.2 ml) of the cleavage solution were withdrawn at regular intervals, filtered, and analyzed by HPLC.

The following Table shows the composition (wt. %) of the cleavage solution at 0 minutes, 15 minutes, and 30 minutes after the addition of the cumene hydroperoxide was complete. The results show 100% conversion of cumene hydroperoxide. The product contained the following components in wt. %, based on the total weight of the cleavage product: less than 0.6 wt. % α-methylstyrene (and dimers); less than 0.2 wt. % acetophenone; only 0.3 wt. % DMBA; and, no dicumylperoxide.

| Fe$_2$O$_3$/WO$_3$ | 0 min. | 15 min. | 30 min. |
|---|---|---|---|
| phenol | 17.70 | 17.75 | 17.70 |
| acetophenone | 0.17 | 0.17 | 0.17 |
| dimethylbenzyl alcohol | 0.62 | 0.47 | 0.30 |
| cumene hydroperoxide | 0.17 | — | — |
| cumyl phenol | — | 0.01 | 0.01 |
| α-methylstyrene | 0.24 | 0.40 | 0.57 |
| Cumene | 4.16 | 4.14 | 4.18 |
| dicumylperoxide | — | — | — |
| dimers | 0.00 | 0.00 | 0.01 |
| % cumene hydroperoxide conversion | 100 | 100 | 100 |

Example 13

To a 250 ml. round bottom flask fitted with a condenser, stirrer, dropping funnel, heating mantle, and temperature regulator for temperature control, was charged a mixture of 100.0 g of acetone and 2.00 g of the Ce-impregnated catalyst prepared in Example 2. The mixture was heated to reflux (57° C.) with stirring, and 50.0 g of (86%) cumene hydroperoxide (CHP) solution (analyzed as 86.1 wt. % CHP, 10.5 wt. % cumene, 3.2 wt. % 2-phenyl-2-propanol, 0.4 wt. % acetophenone) was added dropwise at an approximate rate of 2 g/min. Following addition of the CHP solution, small samples (~0.2 ml) of the cleavage solution were withdrawn at regular intervals, filtered, and analyzed by HPLC.

The following Table shows the composition (wt. %) of the cleavage solution at 0, 15, 30, and 60 minutes after the addition of the CHP was complete. The product contained the following wt. % of the following components, based on the total weight of the cleavage product: 0.16 wt. % acetophenone; less than 0.4 wt. % α-methylstyrene; less than 0.5 wt. % DMBA; 0.02 wt. % or less cumyl phenol; and 1.0 wt. % or less dicumylperoxide.

| CeO$_2$/WO$_3$ | 0 min. | 15 min. | 30 min. | 60 min. |
|---|---|---|---|---|
| Phenol | 16.6 | 17.0 | 17.0 | 17.0 |
| AP | 0.16 | 0.16 | 0.16 | 0.16 |
| DMBA | 0.49 | 0.29 | 0.21 | 0.11 |
| CHP | 0.63 | — | — | — |
| CP | — | 0.01 | 0.01 | 0.02 |
| AMS | 0.11 | 0.2 | 0.27 | 0.39 |
| Cumene | 4.18 | 4.19 | 4.21 | 4.16 |
| DCP | 0.85 | 0.88 | 0.86 | 0.81 |
| Dimers | 0.0 | 0.0 | 0.0 | 0.0 |
| % CHP Conversion | 97.8 | 100.0 | 100.0 | 100.0 |

Example 14

To a 250-ml round bottom flask fitted with a condenser, stirrer, dropping funnel, heating mantle, and temperature regulator for temperature control, was charged a mixture of 100.0 g of acetone and 5.0 g of the catalyst of Example 4. The mixture was heated to reflux (57° C.) with stirring, and 50.0 g of 86% cumene hydroperoxide solution (analyzed as 86.1 wt. % cumene hydroperoxide, 10.5 wt. % cumene, 3.2 wt. % dimethylbenzyl alcohol, 0.4 wt. % acetophenone) was added dropwise at an approximate rate of 2 g/min. Following addition of the cumene hydroperoxide solution, small samples (~0.2 ml) of the cleavage solution were withdrawn at regular intervals, filtered, and analyzed by HPLC.

The following Table shows the composition (mass %) of the cleavage solution at 0 minutes, 15 minutes, 30 minutes, and 60 minutes after the addition of the cumene hydroperoxide was complete. The results show greater than 93% conversion of cumene hydroperoxide. The product contained no α-methylstyrene (or dimers), only 0.1 wt. % acetophenone, and less than 1 wt. % DMBA, based on the total weight of the cleavage product.

| Bi$_2$O$_3$/WO$_3$ | 0 min. | 15 min. | 30 min. | 60 min. |
|---|---|---|---|---|
| phenol | 4.0 | 7.5 | 10.7 | 14.1 |
| acetophenone | 0.1 | 0.1 | 0.1 | 0.1 |
| dimethylbenzyl alcohol | 1.1 | 1.0 | 0.9 | 0.8 |
| cumene hydroperoxide | 19.8 | 11.1 | 6.3 | 1.9 |
| cumyl phenol | 0.0 | 0.0 | 0.0 | 0.0 |
| α-methylstyrene | 0.0 | 0.0 | 0.0 | 0.0 |
| cumene | 3.9 | 3.8 | 3.8 | 3.8 |
| Dicumylperoxide | 0.2 | 0.4 | 0.6 | 0.8 |
| Dimers | 0.0 | 0.0 | 0.0 | 0.0 |
| % cumene hydroperoxide conversion | 31.0 | 61.3 | 78.0 | 93.4 |

Example 15

To a 250-ml round bottom flask fitted with a condenser stirrer and dropping funnel, heating mantle and temperature regulator for temperature control, was charged a mixture of 100.0 g of acetone and 2.00 g of the catalyst produced in Example 5. The mixture was heated to reflux (57° C.) with stirring, and 50.0 g of 86% cumene hydroperoxide solution (analyzed as 86.1 wt. % cumene hydroperoxide, 10.5 wt. % cumene, 3.2 wt. % dimethylbenzyl alcohol, 0.4 wt. % acetophenone) was added dropwise at an approximate rate of 2 g/min. Following addition of the cumene hydroperoxide solution, small samples (~0.2 ml) of the cleavage solution were withdrawn at regular intervals, filtered, and analyzed by HPLC.

The following Table shows the composition (mass %) of the cleavage solution at 0 minutes, 15 minutes, 30 minutes, 60 minutes, and 120 minutes after the addition of the cumene hydroperoxide was complete. The results show 100% conversion of cumene hydroperoxide. The product contained the following components in wt. %, based on the total weight of the cleavage product: 0.05 wt. % α-methylstyrene (and dimers); only 0.13 wt. % acetophenone; and, less than 1 wt. % DMBA.

| ZnO/WO$_3$ | 0 min. | 15 min. | 30 min. | 60 min. | 120 min. |
|---|---|---|---|---|---|
| phenol | 4.74 | 8.39 | 11.64 | 17.45 | 17.46 |
| acetophenone | 0.11 | 0.11 | 0.12 | 0.13 | 0.13 |
| dimethylbenzyl alcohol | 1.05 | 0.97 | 0.89 | 0.76 | 0.64 |
| cumene hydroperoxide | 18.16 | 11.76 | 7.58 | 1.51 | 0 |
| cumyl phenol | — | — | — | — | — |
| α-methylstyrene | 0.01 | 0.01 | 0.02 | 0.05 | 0.05 |
| cumene | 3.80 | 3.87 | 3.83 | 3.97 | 3.85 |
| dicumylperoxide | 0.25 | 0.44 | 0.61 | 0.95 | 0.99 |
| dimers | — | — | — | — | — |
| % cumene hydroperoxide conv. | 36.70 | 59.00 | 73.60 | 94.70 | 100 |

Example 16

To a 250-ml round bottom flask fitted with a condenser, stirrer and dropping funnel, heating mantle and temperature regulator for temperature control, was charged a mixture of 100.0 g of acetone and 5.00 g of the catalyst produced in Example 6. The mixture was heated to reflux (57° C.) with stirring, and 50.0 g of 86% cumene hydroperoxide solution (analyzed as 86.1 wt. % cumene hydroperoxide, 10.5 wt. % cumene, 3.4 wt. % dimethylbenzyl alcohol, 0.4 wt. % acetophenone) was added dropwise at an approximate rate of 2 g/min. Following addition of the cumene hydroperoxide solution, small samples (~0.2 ml) of the cleavage solution were withdrawn at regular intervals, filtered, and analyzed by LG for phenol, cumene hydroperoxide, dimethylbenzyl alcohol, α-methylstyrene, and dimers of α-methylstyrene, dicumyl peroxide, cumylphenol, and acetophenone.

The following Table shows the composition (wt. %) of the cleavage solution at 0 minutes, 60 minutes, and 120 minutes after completion of addition. The results show 100% conversion of cumene hydroperoxide. The product contained the following components in wt. %, based on the total weight of the cleavage product: less than 0.5 wt. % α-methylstyrene (and dimers); only 0.13 wt. % acetophenone; and, less than 0.5 wt. % DMBA.

| ZrO$_2$/SnO$_2$ | 0 min. | 60 min. | 120 min. |
|---|---|---|---|
| phenol | 17.68 | 19.29 | 19.49 |
| acetophenone | 0.12 | 0.13 | 0.13 |
| dimethylbenzyl alcohol | 0.70 | 0.49 | 0.37 |
| cumene hydroperoxide | 0.64 | 0 | 0 |
| cumyl phenol | — | 0.01 | 0.02 |
| α-methylstyrene | 0.08 | 0.3 | 0.42 |
| cumene | 3.73 | 3.99 | 4.01 |
| dicumylperoxide | 0.74 | 0.77 | 0.74 |
| dimers of α-methylstyrene | | | |
| % cumene hydroperoxide conversion | 100 | 100 | 100 |

Example 17

To a 250-ml round bottom flask fitted with a condenser, stirrer, dropping funnel, heating mantle and temperature regulator for temperature control, was charged a mixture of 100.0 g of acetone and 2.00 g of the catalyst produced in Example 7. The mixture was heated to reflux (57° C.) with stirring, and 50.0 g of 86% cumene hydroperoxide solution 655 (analyzed as 86.1 wt. % cumene hydroperoxide, 10.5 wt. % cumene, 3.2 wt. % dimethylbenzyl alcohol, 0.4 wt. % acetophenone) was added dropwise at an approximate rate of 2 g/min. Following addition of the cumene hydroperoxide solution, small samples (~0.2 ml) of the cleavage solution were withdrawn at regular intervals, filtered, and analyzed by HPLC.

The following Table shows the composition (mass %) of the cleavage solution at 60 minutes, 120 minutes, and 180 minutes after the addition of the cumene hydroperoxide was complete. The results show 100% conversion of cumene hydroperoxide. The product contained the following components in wt. %, based on the total weight of the cleavage product: 0.32 wt. % α-methylstyrene (and dimers); only 0.16 wt. % acetophenone; and less than 1 wt. % DMBA.

| Sb$_2$O$_3$/SnO$_2$ | 60 min. | 120 min. | 180 min. |
|---|---|---|---|
| phenol | 9.62 | 19.16 | 19.37 |
| acetophenone | 0.13 | 0.15 | 0.16 |
| dimethylbenzyl alcohol | 1.14 | 0.82 | 0.71 |
| cumene hydroperoxide | 10.59 | 0 | 0 |
| Cumyl phenol | — | 0 | 0 |
| α-methylstyrene | 0.04 | 0.2 | 0.32 |
| cumene | 3.96 | 3.87 | 3.9 |
| dicumylperoxide | 0.57 | 0.06 | 1.11 |
| Dimers of α-methylstyrene | 0.01 | — | — |
| % cumene hydroperoxide conversion | 100 | 100 | 100 |

Example 18

Experimental Procedure

In order to confirm that the solid cleavage catalysts would be effective for use where the cleavage reaction mixture comprises less ketone and a higher concentration of cumene hydroperoxide, the following procedure was performed using a bench scale unit adaptable for continuous operation, schematically illustrated in FIG. 1. Only one stage is shown in FIG. 1, but the bench scale unit actually included two stages. In a first stage (shown in FIG. 1), phenylalkyl hydroperoxides were cleaved to produce a cleavage product comprising di(phenylalkyl)peroxide as a byproduct. In a second stage the di(phenylalkyl)peroxide byproduct was decomposed. The bench scale unit was run over a period of several days.

Referring to FIG. 1, in the bench scale unit the cleavage reactor 12 was a column reactor. At any given time, the total volume of reaction mixture in the cleavage reactor 12 was approximately 250 ml. Cumene hydroperoxide 82-86 wt. % was added to the recycle loop 16 at point 26 using a dual set of 250 ml capacity Isco pumps (see 14) equipped for continuous and accurate feed control. The temperature in the cleavage reactor 12 was controlled by regulating the steam to the heat exchanger 18. Once the reaction started, the reaction was controlled by heat exchanger 18, feed rate, and recycle rate. The temperature was measured across the cleavage reactor 12, as indicated at 34-34'. In order to analyze the cleavage product and to adjust reaction conditions, the cleavage product was sampled at a first sampling port 30. The sampled cleavage product was analyzed once a day using high performance liquid chromatography (HPLC).

The tin/tungsten catalyst of Example 1 was packed in the cleavage column 12. The feed to the cleavage column 12 comprised 86 wt. % cumene hydroperoxide containing 9.6 wt. % cumene, 3.6 wt. % dimethylbenzylalcohol, 0.4 wt. % acetophenone, and 0.2 wt. % dicumylperoxide.

The feed rate was 100 g total feed/hour and the recycle rate through line 16 was 4000 g/hour. The temperature near the top (34) of the cleavage column 12 was 60° C. The ΔT, or temperature difference across the column (34-34' in FIG. 1) was 10-11° C. The cleavage product (line 20) was sampled once a day via sampling port 30. The following Table shows the analysis of minor components of the cleavage product for 138 hours. (The remainder being acetone and phenol). The amount of acetophenone remained constant at 0.4% wt.

| Time hrs. | dimethylbenzyl alcohol wt % | cumene hydro-peroxide wt % | cumyl phenol wt % | α-methyl-styrene wt % | cumene wt % | dicumyl-peroxide wt % | dimers of α-methyl-styrene wt % |
|---|---|---|---|---|---|---|---|
| 0 | 0.26 | 0.0 | 0.27 | 1.83 | 9.47 | 1.13 | 0.3 |
| 18 | 0.26 | 0.72 | 0.40 | 1.54 | 8.39 | 1.35 | 0.3 |
| 42 | 0.36 | 1.53 | 0.31 | 1.47 | 8.76 | 2.18 | 0.2 |
| 66 | 0.50 | 2.59 | 0.23 | 1.42 | 9.82 | 3.24 | 0.1 |
| 90 | 0.60 | 3.73 | 0.17 | 1.23 | 10.00 | 3.88 | 0.1 |
| 114 | 0.61 | 3.79 | 0.13 | 0.98 | 9.15 | 3.84 | 0.1 |
| 138 | 0.61 | 3.68 | 0.21 | 1.48 | 10.11 | 3.84 | 0.1 |

The cleavage product was fed to a second stage, which resulted in AMS selectivity of from 0.71 to 0.80 depending upon the conditions in the second stage.

The foregoing demonstrates that the cleavage catalyst is effective to cleave cumene hydroperoxide present in the cleavage reaction mixture at relatively high concentrations. Feeding a ketone feed to the cleavage reaction mixture is expected to further reduce the concentration of the byproducts cumyl phenol and dimers of α-methyl-styrene.

Persons of ordinary skill in the art will recognize that many modifications may be made to the foregoing description. The embodiments described herein are meant to be illustrative only and should not be taken as limiting the invention, which will be defined in the claims.

What is claimed is:

1. A catalyst consisting essentially of:
   a combination comprising a first amount of oxidized first metal and a second amount of oxidized second metal;
   wherein the first metal is selected from the group consisting of tin, zinc, bismuth, and combinations thereof and the second metal is selected from the group consisting of zirconium, antimony, and combinations thereof.

2. The catalyst of claim 1 wherein the combination has an acidity greater than that of a mixture formed by separately oxidizing the first metal and the second metal and subsequently mixing the first amount of the oxidized first metal with the second amount of the oxidized second metal.

3. The catalyst of claim 2 wherein the first metal is tin and the second metal is zirconium.

4. The catalyst of claim 3 comprising 5 wt. % tin (IV) and 10 wt. % zirconium.

5. The catalyst of claim 1 further comprising a support.

6. The catalyst of claim 3 further comprising a support.

7. A catalyst comprising oxidized forms of a combination of metals selected from the group consisting of: zirconium and tin; and, antimony and tin.

8. The catalyst of claim 7 wherein the combination of oxidized metals has an acidity greater than that of a mixture formed by separately oxidizing each metal and subsequently mixing the same quantity of oxidized metals to form the mixture.

9. The catalyst of claim 8 further comprising a support.

10. A process for cleaving phenylalkyl hydroperoxides comprising subjecting a feed comprising one or more phenylalkyl hydroperoxides to a catalyst composition
   comprising a catalyst consisting essentially of:
   a combination comprising a first amount of oxidized first metal and a second amount of oxidized second metal;
   wherein the first metal is selected from the group consisting of tin, zinc, bismuth, and combinations thereof and
   the second metal is selected from the group consisting of zirconium, antimony, tungsten, and combinations thereof
   under cleavage conditions which cleave the phenylalkyl hydroperoxides and produce a cleavage product comprising one or more hydroxybenzenes and one or more ketones.

11. A process for cleaving phenylalkyl hydro-peroxides comprising:
   feeding a phenylalkyl hydroperoxide feed and a ketone feed to a reactor in a continuous process to produce a cleavage reaction mixture, the reactor containing catalyst consisting essentially of a combination of oxidized metals wherein the first metal is selected from the group consisting of tin, zinc, bismuth, and combinations thereof and the second metal is selected from the group consisting of zirconium, antimony, tungsten, and combinations thereof; and
   subjecting the cleavage reaction mixture to cleavage conditions in the presence of the catalyst, the cleavage conditions being effective to cleave phenylalkyl hydroperoxide and to produce a cleavage product comprising one or more hydroxybenzenes and one or more ketones.

12. The process of claim 11 wherein the phenylalkyl hydroperoxide feed comprises a first concentration of one or more di(phenylalkylperoxides) of 0 wt. % or greater, and the cleavage conditions and the catalyst produce a second concentration of the one or more di(phenylalkyl)peroxides which is greater than the first concentration.

13. The process of claim 11 further comprising recovering ketone from the cleavage product and recycling the ketone to the cleavage reaction mixture as the ketone feed.

14. The process of claim 13 wherein the phenylalkyl hydroperoxide feed is fed to the reactor at a phenylalkyl hydroperoxide feed rate, the process further comprising feeding ketone feed at a ketone feed rate of from 0.1 wt. % to 10 wt. % based on the phenylalkyl hydroperoxide feed rate.

15. The process of claim 11 wherein the cleavage conditions comprise:
a cleavage temperature of from 50° C. to 90° C. and a cleavage pressure of from 15 kPa to 7000 kPa;
recycling cleavage product to the cleavage feed at a ratio of recycled cleavage product to cleavage feed of from 10:1 to 100:1 on a weight basis; and,
a liquid hourly space velocity of from 0.1 to 100 $hr^{-1}$, based on the concentration of phenylalkyl hydroperoxide.

16. The process of claim 14 wherein the cleavage conditions comprise:
a cleavage temperature of from 50° C. to 90° C. and a cleavage pressure of from 15 kPa to 7000 kPa;
recycling cleavage product to the cleavage feed at a ratio of recycled cleavage product to cleavage feed of from 10:1 to 100:1 on a weight basis; and,
a liquid hourly space velocity of from 0.1 to 100 $hr^{-1}$, based on the concentration of phenylalkyl hydroperoxide.

17. The process of claim 16 wherein
the ratio of recycled cleavage product to cleavage feed is from 20:1 to 40:1 on a weight basis;
the liquid hourly space velocity is from 20 to 60 $hr^{-1}$.

18. The process of claim 17 wherein the process is run under adiabatic conditions.

* * * * *